United States Patent [19]

Kehne et al.

[11] Patent Number: 5,272,129
[45] Date of Patent: Dec. 21, 1993

[54] PHENOXYSULFONYLUREAS BASED ON 3-SUBSTITUTED ALKYL SALICYLATES, AND THEIR USE AS HERBICIDES AND PLANT GROWTH REGULATORS

[75] Inventors: Heinz Kehne, Hofheim am Taunus; Lothar Willms, Hillscheid; Klaus Bauer, Hanau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main

[21] Appl. No.: 973,213

[22] Filed: Nov. 6, 1992

Related U.S. Application Data

[63] Continuation of Ser. No. 495,266, Mar. 16, 1990, abandoned.

[30] Foreign Application Priority Data

Mar. 18, 1989 [DE] Fed. Rep. of Germany ....... 3909053

[51] Int. Cl.$^5$ .................... A01N 43/54; C07D 239/69
[52] U.S. Cl. .................................. 504/214; 544/332; 544/321
[58] Field of Search ................ 544/321, 332; 504/214

[56] References Cited

U.S. PATENT DOCUMENTS

| | | | |
|---|---|---|---|
| 4,191,553 | 3/1980 | Reap | 71/92 |
| 4,391,976 | 7/1983 | Boehner | 544/211 |
| 4,480,101 | 10/1984 | Meyer | 544/320 |

FOREIGN PATENT DOCUMENTS

| | | |
|---|---|---|
| 0004163 | 9/1979 | European Pat. Off. |
| 0044807 | 1/1982 | European Pat. Off. |
| 0141199 | 5/1985 | European Pat. Off. |
| 0342569 | 11/1987 | European Pat. Off. |
| 3151450 | 7/1983 | Fed. Rep. of Germany |
| 3725939 | 2/1989 | Fed. Rep. of Germany |
| 89/3643 | 11/1987 | South Africa |
| 88/5725 | 2/1989 | South Africa |
| 2133790 | 8/1984 | United Kingdom |

OTHER PUBLICATIONS

Chem. Ber. 105 "Darstellung und Umsetzungen von Aryloxysulfonylisocyanaten", Gerhard Lohaus, p. 2791, (1972).

*Primary Examiner*—John M. Ford
*Attorney, Agent, or Firm*—Curtis, Morris & Safford

[57] ABSTRACT

Compounds of the formula (I) or salts thereof

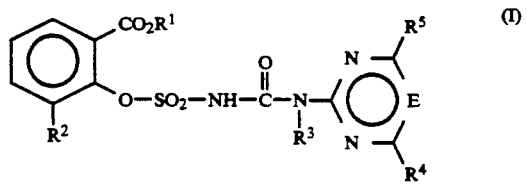

in which
$R^1$ is $(C_1-C_4)$alkyl, $R^2$ is halogen, methoxy, ethyl or propyl, $R^3$ is hydrogen or methyl, E is CH or N and $R^4$ and $R^5$ independently of one another are halogen, $(C_1-C_4)$alkyl, $(C_1-C_4)$alkoxy or $(C_1-C_4)$alkylthio, the abovementioned alkyl-containing radicals being unsubstituted or substituted by one or more halogen atoms or one or two $(C_1-C_4)$alkoxy or $(C_1-C_4)$alkylthio groups, have an excellent herbicidal action against a large number of harmful plants and also growth-regulatory properties on plants.

16 Claims, No Drawings

PHENOXYSULFONYLUREAS BASED ON 3-SUBSTITUTED ALKYL SALICYLATES, AND THEIR USE AS HERBICIDES AND PLANT GROWTH REGULATORS

This application is a continuation of application Ser. No. 07/495,266, filed Mar. 16, 1990 now abandoned.

DESCRIPTION

It is known that phenoxysulfonylureas containing heterocyclic substituents have herbicidal and plant growth-regulating properties (EP-A-4,163, DE-A-3,151,450, DE-A-3,725,939 (ZA-88/5725) and German Patent Application P-3,816,704.2 (EP-A-0,342,569, and ZA-89/3643)).

EP-A-4,163 thus describes, inter alia, 2-methoxyphenoxy-, 2-chlorophenoxy- and 2-alkylphenoxy- as well as 2-carbomethoxy-phenoxysulfonylureas having a herbicidal action.

Surprisingly, it has now been found that combinations of the carbomethoxy substituents with in each case one of the other radicals mentioned leads to a considerable improvement in the herbicidal properties.

The present invention thus relates to compounds of the formula (I) or salts thereof

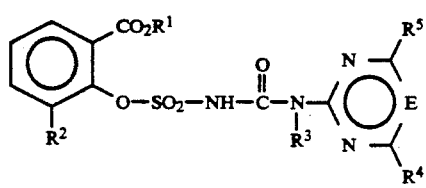

in which
R$^1$ is (C$_1$-C$_4$) alkyl,
R$^2$ is halogen, methoxy, ethyl or propyl,
R$^3$ is hydrogen or methyl,
E is CH or N and
R$^4$ and R$^5$ independently of one another are halogen, (C$_1$-C$_4$) alkyl, (C$_1$-C$_4$) alkoxy or (C$_1$-C$_4$) alkylthio, the abovementioned alkyl-containing radicals being unsubstituted or substituted by one or more halogen atoms or one or more (C$_1$-C$_4$)alkoxy or (C$_1$-C$_4$)alkylthio groups.

Halogen is fluorine, chlorine, bromine and/or iodine, preferably fluorine, chlorine and/or bromine, in particular fluorine or chlorine.

(C$_1$-C$_4$)alkyl and the corresponding alkyl radical in the alkyl-containing radicals, such as alkoxy or alkylthio, is methyl, ethyl, n-propyl, i-propyl, n-butyl, i-butyl, t-butyl or 2-butyl.

The compounds of the formula I can form salts in which the hydrogen of the —SO$_2$—NH group is replaced by a cation suitable for agriculture. These salts are in general metal salts, in particular alkali metal or alkaline earth metal salts, and if appropriate inorganic or organic ammonium salts.

Preferred compounds of the formula I or salts thereof are those in which R$^1$ is methyl or ethyl, E is a group of the formula CH and R$^4$ and R$^5$ independently of one another are chlorine, bromine, (C$_1$-C$_2$)alkyl or (C$_1$-C$_4$)alkoxy, it being possible for the abovementioned alkyl-containing radicals to be substituted by one or more fluorine or chlorine atoms.

Particularly preferred compounds of the formula I or salts thereof are those in which R$^1$ is methyl or ethyl, E is a group of the formula CH and R$^4$ and R$^5$ independently of one another are chlorine, (C$_1$-C$_2$)alkyl or (C$_1$-C$_2$)alkoxy, it being possible for the abovementioned alkyl-containing radicals to be substituted by one or more fluorine or chlorine atoms.

The present invention furthermore relates to processes for the preparation of the compounds of the general formula I or salts thereof, which comprise a) reacting a compound of the formula (II)

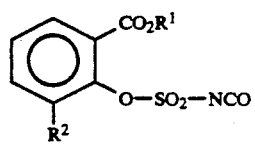

with a compound of the formula (III)

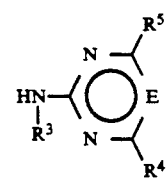

or b) reacting a compound of the formula (IV)

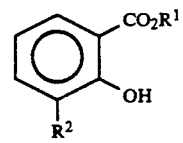

with a chlorosulfonylurea of the formula (V)

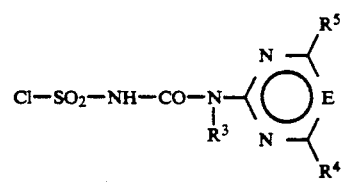

or c) reacting a compound of the formula (VI)

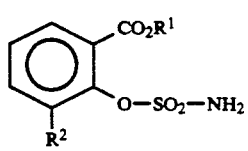

with a carbamate of the formula (VII)

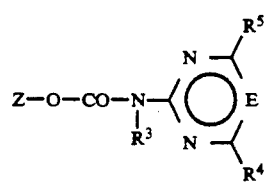

in which Z is phenyl or $(C_1-C_6)$ alkyl, and if appropriate converting the resulting compounds of the formula (I) into their salts.

The reaction of the compounds of the formulae (II) and (II) is preferably carried out in inert aprotic solvents, such as, for example, acetonitrile, methylene chloride, toluene, chlorobenzene, tetrahydrofuran or dioxane,, at temperatures between 0° C and the boiling point of the solvent.

The phenoxysulfonyl isocyanates of the formula (II) can be prepared in a simple manner by processes which are known in principle from the corresponding salicylic acid esters of the formula (IV) and chlorosulfonyl isocyanate (c.f. G. Lohaus, Chem. Ber. 105, 2791 (1972)).

The starting substances of the formula (III) are known or can be prepared by processes which are known in principle, for example by cyclization of corresponding guanidine derivatives with correspondingly substituted 1,3-diketones, c.f., for example, "The Chemistry of Heterocyclic Compounds". Vol. XVI (1962) and Supplement I (1970), or by derivatization of cyanuric chloride, c.f., for example, "The Chemistry of Heterocyclic Compounds", L. Rapaport: "s-Triazines and Derivatives" (1959)).

The reaction of the compounds of the formula (IV) with the chlorosulfonylureas of the formula (V) is preferably carried out in inert solvents, such as, for example, methylene chloride, tetrahydrofuran, dioxane or dimethoxyethane, at temperatures between −10° C. and 80° C. in the presence of a base as the HCl-binding agent. Bases which can be employed are alkali metal carbonates or bicarbonates and alkaline earth metal carbonates or bicarbonates, such as, for example, $K_2CO_3$, $NaHCO_3$ and $Na_2CO_3$ or tertiary amines, such as, for example, pyridine or triethylamine.

The salicylic acid eaters of the formula (IV) are known from the literature or can be prepared by processes which are known from the literature. The chlorogulfonylureas of the formula (V) are accessible from the amines of the formula (III) and chlorosulfonyl isocyanate (EP-A 141,199).

The reaction of the compounds of the formula (VI) with the heterocyclic carbamates of the formula (VII) is preferably carried out in the presence of tertiary organic bases such as, for example, 1,8-diazabicyclo[5.4.0]-undec-7-ene (DBU) in inert solvents, such as acetonitrile or dioxane, at temperatures between 20° C. and the boiling point of the solvent (analogously to EP-A 44,807).

The carbamates of the formula (VII) required for this reaction are known from the literature or are prepared by known processes (EP-A 70,,804). The sulfamates of the formula (VI) are prepared by known processes from the salicylic acid esters on which they are based (c.f., for example, Synthesis 1978, 357; Z. Chem. 15, 270 (1975) and Chem. Ber. M , 2791 (1972)).

The salts of the compounds of the formula (I) are preferably prepared in inert solvents, such as, for example, water, methanol or acetone, at temperatures of 0°-100° C. Examples of suitable bases for the preparation of the salts according to the invention are alkali metal carbonates, such as potassium carbonate, alkali metal and alkaline earth metal hydroxides, ammonia or ethanolamine.

The compounds of the formula I according to the invention have an excellent herbicidal activity against a broad spectrum of economically important mono- and dicotyledon harmful plants. Even perennial weeds which are difficult to combat and shoot from rhizomes, rootstock or other permanent organs are readily affected by the active compounds. It is irrelevant here whether the substances are applied by the pre-sowing, pre-emergence or post-emergence method. Some representatives of the mono- and dicotyledon weed flora which can be controlled by the compounds according to the invention may be mentioned as examples, without the list representing a limitation to certain species.

On the part of monocotyledon weed species,, examples which are readily affected are Avena, Lolium, Alopecurus, Phalaris, Echinochloa, Digitaria, Setaria and the like, as well as Cyperus species from the annual group, and on the part of perennial species Agropyron, Cynodon, Imperata and Sorghum and the like, and also perennial Cyperus species.

In the case of dicotyledon weed species, the action spectrum extends to Galium, Viola, Veronica, Lamium, Stellaria, Amaranthus, Sinapis, Ipomoea, Matricaria, Abutilon, Sida and the like on the annual side, and Convolvulus, Cirsium, Rumex, Artemisia and the like amongst the perennial weeds.

Weeds which occur under the specific crop conditions in rice, such as, for example, Sagittaria, Alisma, Eleocharis, Scirpus, Cyperus and the like, are also controlled outstandingly well by the active compounds according to the invention.

If the compounds according to the invention are applied to the soil surface before germination, either emergence of the weed seedlings is prevented completely, or the weeds grow to the cotyledon stage, but then stop growing and finally die completely after a period of three to four weeks.

If the active compounds are applied to the green parts of plants by the post-emergence process, a drastic stop in growth likewise occurs very rapidly after the treatment, and the weed plants remain in the growth stage which existed at the time of application, or die more or less rapidly after a certain period of time, so that weed competition which is damaging to the crop plants can in this way be eliminated very early and in a lasting manner by using the novel agents according to the invention.

Although the compounds according to the invention have an excellent herbicidal activity against mono- and dicotyledon weeds, crop plants of economically important crops, such as, for example, wheat, barley, rye, rice, maize, sugar beet, cotton and soya, are harmed only insignificantly, if at all. For these reasons, the present compounds are particularly suitable for selectively controlling undesirable plant growth in agricultural crop plantations.

The compounds according to the invention moreover exhibit growth-regulatory properties in crop plants. They intervene in a regulating manner in the endogenous metabolism of the plant and can therefore be employed for facilitating harvesting, such as, for example, by inducing desiccation, abscission and growth compression. They are moreover also suitable for the general control and inhibition of undesirable vegetative growth, without at the same time killing the plants. An inhibition of vegetative growth is of great importance in many mono-and dicotyledon crops, since lodging can in this way be reduced or completely prevented.

The compounds of the formula (I) can be formulated in various ways, according to the biological and/or chemicophysical parameters which exist. Examples of suitable formulation possibilities are: wettable powders (wp), emulsifiable concentrations (EC) and aqueous solutions (SL); emulsions, sprayable solutions, oil- or water-based dispersions (SC), suspoemulsions, dusting agents (DP), dressing agents, granules (GR), such as soil or scattering granules (FG) or water-dispersible granules (WG), ULV formulations, microcapsules or waxes.

These individual types of formulations are known in principle and are described, for example, in: Winnacker-Küchler, "Chemische Technologie (Chemical Technology)" Vol. 7, C. Hauser Verlag Munich, 4th Edition, 1986; van Falenkenberg, "Pesticides Formulations", Marcel Dekker, N.Y., 2nd Edition, 1972-73; and K. Martens, "Spray Drying Handbook", 3rd Edition, 1979, G. Goodwin Ltd., London.

The formulation auxiliaries required, such as inert materials, surfactants, solvents and other additives, are likewise known and are described, for example, in: "Handbook of Insecticide Dust Diluents and Carriers", 2nd Edition, Darland Books, Caldwell N.J.; H. V. Olphen, "Introduction to Clay Colloid Chemistry"; 2nd Edition, J. Wiley & Sons, N.Y.; Marschen, "Solvents Guide", 2nd Edition, Interscience, N.Y., 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y., 1964; Schönfeldt, "Grenzflächenaktive Äthylenoxidaddukte (Surface-active ethylene oxide adducts)", Wiss. Verlagsgesell., Stuttgart 1976; Winnacker-Küchler, "Chemische Technologie (Chemical Technology)", Volume 7, C. Hauser Verlag Munich, 4th Edition, 1986.

Wettable powders are preparations which are uniformly dispersible in water and which, in addition to the active compounds, and if appropriate in addition to a diluent or inert substance, also contain wetting agents, for example polyoxyethylated alkylphenole, polyoxyethylated fatty alcohols and fatty amines, alkane sulfonates or alkylaryl sulfonates, such as alkylbenzenesulfonates, and dispersing agents, for example sodium ligninsulfonate, sodium 2,2'-dinaphthylmethane-6,6''-disulfonate, sodium dibutylnaphthalenesulfonate or sodium oleoyl-methyl-taurate. They are prepared in the customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatics or hydrocarbons, with the addition of one or more emulsifiers. If the active compounds are liquid, all or some of the solvent content can also be dispensed with. Examples of emulsifiers which can be used are: calcium alkylarylsulfonates, such as Ca dodecylbenzenesulfonate, or nonionic emulsifiers, such as fatty acid polyglycol esters, alkyl-aryl polyglycol ethers, fatty alcohol polyglycol ethers, propylene oxide-ethylene oxide condensation products, fatty alcohol-propylene oxide-ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active compound with finely divided solid substances, for example talc or natural clays, such as kaolin, bentonite, pyrophyllite or diatomaceous earth.

Granules can be prepared either by spraying the active compound on to an absorbent granular inert material or by applying active compound concentrates to the surface of carriers, such as sand or kaolinites, or of granular inert material by means of binders, for example polyvinyl alcohol, sodium polyacrylate or mineral oils. Suitable active compounds can also be granulated in the manner customary for the preparation of fertilizer granules, if desired as a mixture with fertilizers.

The agrochemical formulations as customary contain 0.1 to 99% by weight, in particular 2 to 95% by weight, of active compound of the formula (I). The concentrations of the active compound can vary here, depending on the type of formulation.

In wettable powders, the active compound concentration is, for example, about 10 to 90% by weight, the remainder to make up to 100% by weight consisting of customary formulation constituents. In emulsifiable concentrates, the active compound concentration can be about 5 to 80% by weight. Dust-like formulations usually contain 5 to 20% by weight, and sprayable solutions about 2 to 20% by weight. In granules, the active compound content depends in part on whether the active compound is in liquid or solid form and on what granulation auxiliaries, fillers and the like are used.

In addition, the active compound formulations mentioned contain, if appropriate, the particular customary adhesives, wetting agents, dispersing agents, emulsifiers, penetration agents, solvents, fillers or carriers is or mixtures thereof.

The invention thus also relates to herbicidal and plant growth-regulating agents which contain a compound of the formula (I) or salts thereof and customary formulation auxiliaries which are inert under the storage conditions.

For use, the concentrates in the commercially available form are diluted, if appropriate, in the customary manner, for example by means of water in the case of wettable powders, emulsifiable concentrates, dispersions and in some cases also microgranules. Dust-like and granular formulations and sprayable solutions are usually not diluted further with additional inert substances before use.

The application amount required varies in accordance with the external conditions, such as temperature, humidity and the like. It can vary within wide limits, for example between 0.005 and 10.0 kg/ha or more of active substance, but is preferably between 0.01 and 5 kg/ha.

Mixtures or mixed formulations with other active compounds, such as, for example, insecticides, acaricides, herbicides, fertilizers, growth regulators or fungicides, are also possible if appropriate.

The invention is explained in more detail by the following Examples.

FORMULATION EXAMPLES

A. A dusting agent is obtained by mixing 10 parts by weight of active compound with 90 parts by weight of talc or a comparable inert substance and comminuting the mixture in an impact mill.

B. A wettable powder which is readily dispersible in water is obtained by mixing 25 parts by weight of active compound, 64 parts by weight of kaolin-containing quartz, as the inert substance, 10 parts by weight of potassium ligninsulfonate and 1 part by weight of sodium oleoyl-methyl-taurates, as the wetting and dispersing agent, and grinding the mixture in a pinned disk mill.

C. A dispersion concentrate which is readily dispersible in water is obtained by mixing 20 parts by weight of active compound with 6 parts by weight of alkylphenol polyglycol ether (®Triton X 207), 3 parts by weight of isotridecanol polyglycol ether (8 mol of ethylene oxide) and 71 parts by weight of paraffinic mineral oil (boiling range, for example, about 255° to more than 377° C.), and grinding the mixture to a fineness of less than 5 microns in a bead mill.

D. An emulsifiable concentrate is obtained from 15 parts by weight of active compound, 75 parts by weight of cyclohexanone, as the solvent, and 10 parts by weight of oxyethylated nonylphenol (10 mol of ethylene oxide), as the emulsifier.

E. Water-dispersible granules are obtained by mixing

| |
|---|
| 75 parts by weight of a compound of the formula (I), |
| 10 parts by weight of calcium ligninsulfonate, |
| 5 parts by weight of sodium laurylsulfate, |
| 3 parts by weight of polyvinyl alcohol and |
| 7 parts by weight of kaolin, | grinding the mixture on a pinned disk mill and granulating the powder in a fluidized bed by spraying on water as the granulating liquid.

F. Water-dispersible granules are also obtained by homogenizing and precomminuting

| |
|---|
| 25 parts by weight of a compound of the formula (I), |
| 5 parts by weight of sodium 2,2'-dinaphthylmethyl-6,6'-disulfonate |
| 2 parts by weight of sodium oleolyl-methyl-taurate, |
| 1 parts by weight of polyvinyl alcohol, |
| 17 parts by weight of calcium carbonate and |
| 50 parts by weight of water | on a colloid mill, subsequently grinding the mixture on a bead mill, atomizing the resulting suspension in a spray tower by means of a one-component jet and drying the product.

G. Extruded granules are obtained by mixing

| |
|---|
| 20 parts by weight of active compound, |
| 3 parts by weight of sodium ligninsulfonate, |
| 1 parts by weight of carboxymethylcellulose and |
| 76 parts by weight of kaolin, | grinding the mixture and moistening it with water. This mixture is extruded and then dried in a stream of air.

CHEMICAL EXAMPLES

Example 1 (precursor)

Methyl-2-isocyanatosulfonyloxy-3-methoxy-benzoate 3.4 g (0.024 mol) of chlorosulfonyl isocyanate are added dropwise to a solution of 3.6 g (0.02 mol) of methyl 3-methoxy-salicylate in 20 ml of xylene at 25° C. When the dropwise addition has ended, the temperature is slowly increased to 140° C. and the mixture is heated under reflux for 2.5 hours. It is cooled and the solvent and excess chlorosulfonyl isocyanate are removed on a rotary evaporator. The yellow oil which remains (5.4 g=100% of theory) is used without further purification.

Example 2

Methyl 2-[3-(4,6-dinethoxypyrisidin-2-yl)-ureidosulfonyloxy]-3-methoxy-benzoate (formula I where $R^1=CH_3$, $R^2=OCH_3$, $R^3=H$, $R^4=OCH_3$, $R^5=OCH_3$ and $E=CH$)

A solution of 5.4 g (0.02 mol) of the product from Example 1 in 10 ml of methylene chloride is added dropwise to 3.1 g (0.02 mol) of 2-amino-4,6-dimethoxypyrimidine in 50 ml of methylene chloride at 0° C. The mixture is subsequently stirred at 25° C. for 24 hours and diluted with 50 ml of methylene chloride and the organic phase is washed twice with 50 ml of 2N hydrochloric acid each time and once with 50 ml of water. After drying with sodium sulfate and removing the solvent on a rotary evaporator, an oily product remains, which crystallizes on trituration with diethylether. 6.8 g (77% of theory) of methyl 2-[3-(4,6-dimethoxypyrimidin-2-yl)-ureidosulfonyloxy]-3-methoxy-benzoate of melting point 169°-170° C. are obtained.

Example 3

Methyl 2-[3-(4-chloro-6-methylpyrimidin-2-yl)-ureidosulfonyloxy]-3-methoxy-benzoate (Formula I where $R^1=CH_3$, $R^2=OCH_3$, $R^3=H$, $R^4=Cl$ $R^5=CH_3$, and $E=CH$)

A solution of 5.4 g (0.02 mol) of the product from Example 1 in 10 ml of methylene chloride is added dropwise to 2.9 g (0.02 mol) of 2-amino-4-chloro-6-methylpyrimidine in 50 ml of methylene chloride at 0° C. The mixture is subsequently stirred at 25° C. for 24 hours and diluted with 50 ml of methylene chloride, and the organic phase is washed twice with 50 ml of 2N hydrochloric acid each time and once with water. After drying with sodium sulfate and removing the solvent on a rotary evaporator, an oily product remains, which crystallizes on trituration with diisopropylether. 7.8 g (91% of theory of methyl 2-[3-(4-chloro-6-methyl-pyrimidin-2-yl)-ureidosulfonyloxy]-3-methoxybenzoate of melting point 140°-143° C. are obtained.

The compounds listed below in Table 1 can be prepared as describer in Examples 1-3.

TABLE 1

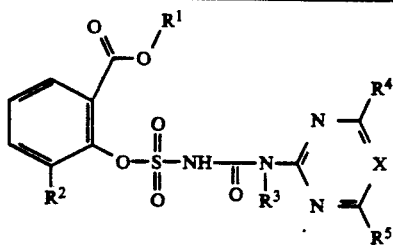

| Example No. | $R^1$ | $R^2$ | $R^3$ | $R^4$ | $R^5$ | X | Melting Point [°C.] |
|---|---|---|---|---|---|---|---|
| 4 | $CH_3$ | $OCH_3$ | H | $CH_3$ | $CH_3$ | CH | 144–145 |
| 5 | " | " | H | $OCH_3$ | $CH_3$ | CH | 147–149 |
| 6 | " | " | H | $CH_3$ | $CH_3$ | N | |
| 7 | " | " | H | $OCH_3$ | $CH_3$ | N | 160–161 |
| 8 | " | " | H | $OCH_3$ | $OCH_3$ | N | |
| 9 | " | " | H | $OCH_3$ | Cl | CH | 130–133 |
| 10 | " | " | H | $OCF_2H$ | $CH_3$ | CH | |
| 11 | " | " | H | $OCF_2H$ | $OCF_2H$ | CH | |
| 12 | " | " | H | $OCH_3$ | Br | CH | |
| 13 | " | " | H | $OCH_3$ | $OC_2H_5$ | CH | |
| 14 | " | " | H | $OCH_3$ | $SCH_3$ | CH | |
| 15 | " | " | H | $OCH_3$ | $OC_2H_5$ | N | |
| 16 | " | " | H | $OCH_3$ | $OC_3H_7$ | CH | |
| 17 | " | " | H | $OCH_3$ | Cl | N | |
| 18 | " | " | H | Cl | $OC_2H_5$ | CH | |
| 19 | " | " | H | $OC_2H_5$ | $OC_2H_5$ | CH | |
| 20 | " | " | H | $C_2H_5$ | $OCH_3$ | CH | |
| 21 | " | " | H | $CF_3$ | $OCH_3$ | CH | |
| 22 | " | " | H | $OCH_2CF_3$ | $CH_3$ | CH | |
| 23 | " | " | H | $OCH_2CF_3$ | $OCH_3$ | CH | |
| 24 | " | " | H | $OCH_2CF_3$ | $OCH_2CF_3$ | CH | |
| 25 | " | " | H | $OCH_2CF_3$ | $OCH_3$ | N | 143–144 |
| 27 | " | " | H | $OCH_3$ | $CH(OCH_3)_2$ | CH | |
| 28 | $C_2H_5$ | " | H | $OCH_3$ | $OCH_3$ | CH | |
| 29 | " | " | H | $OCH_3$ | $CH_3$ | CH | |
| 30 | " | " | H | $CH_3$ | $CH_3$ | CH | |
| 31 | " | " | H | $OCH_3$ | Cl | CH | |
| 32 | " | " | H | $OCH_3$ | $OCH_3$ | N | |
| 33 | " | " | H | $OCH_3$ | $CH_3$ | N | |
| 34 | $C_3H_7$ | " | H | $OCH_3$ | $OCH_3$ | CH | |
| 35 | " | " | H | $OCH_3$ | $CH_3$ | CH | |
| 36 | " | " | H | $OCH_3$ | $CH_3$ | N | |
| 37 | $C_4H_9$ | " | H | $OCH_3$ | $OCH_3$ | CH | 129 |
| 38 | " | " | H | $OCH_3$ | $CH_3$ | CH | 118–119 |
| 39 | " | " | H | $OCH_3$ | $CH_3$ | N | |
| 40 | $CH_3$ | " | $CH_3$ | $OCH_3$ | $OCH_3$ | CH | 144–145 |
| 41 | " | " | $CH_3$ | $OCH_3$ | $CH_3$ | CH | |
| 42 | " | " | $CH_3$ | $OCH_3$ | $CH_3$ | N | 100–103 |
| 43 | " | " | $CH_3$ | $OCH_3$ | Cl | CH | |
| 44 | " | " | $CH_3$ | $OCF_2H$ | $OCF_2H$ | CH | |
| 45 | " | " | $CH_3$ | $CH_3$ | $CH_3$ | CH | |
| 46 | $C_2H_5$ | " | $CH_3$ | $OCH_3$ | $OCH_3$ | CH | |
| 47 | " | " | $CH_3$ | $OCH_3$ | $CH_3$ | CH | |
| 48 | $CH_3$ | Cl | H | $CH_3$ | $CH_3$ | CH | |
| 49 | " | " | H | $OCH_3$ | $CH_3$ | CH | 92–95 (Decomposition) |
| 50 | " | " | H | $CH_3$ | $CH_3$ | N | |
| 51 | " | " | H | $OCH_3$ | $CH_3$ | N | |
| 52 | " | " | H | $OCH_3$ | $OCH_3$ | N | |
| 53 | " | " | H | $OCH_3$ | Cl | CH | |
| 54 | " | " | H | $OCF_2H$ | $CH_3$ | CH | |
| 55 | " | " | H | $OCF_2H$ | $OCF_2H$ | CH | |
| 56 | " | " | H | $OCH_3$ | Br | CH | |
| 57 | " | " | H | $OCH_3$ | $OC_2H_5$ | CH | |
| 58 | " | " | H | $OCH_3$ | $SCH_3$ | CH | |
| 59 | " | " | H | $OCH_3$ | $OC_2H_5$ | N | |
| 60 | " | " | H | $OCH_3$ | $OC_3H_7$ | CH | |
| 61 | " | " | H | $OCH_3$ | Cl | N | |
| 62 | " | " | H | Cl | $OC_2H_5$ | CH | |
| 63 | " | " | H | $OC_2H_5$ | $OC_2H_5$ | CH | |
| 64 | " | " | H | $C_2H_5$ | $OCH_3$ | CH | |
| 65 | " | " | H | $CF_3$ | $OCH_3$ | CH | |
| 66 | " | " | H | $OCH_2CF_3$ | $CH_3$ | CH | |
| 67 | " | " | H | $OCH_2CF_3$ | $OCH_3$ | CH | |
| 68 | " | " | H | $OCH_2CF_3$ | $OCH_2CF_3$ | CH | |
| 69 | " | " | H | $OCH_2CF_3$ | $OCH_3$ | N | |
| 70 | " | " | H | $OCH_3$ | $CH(OCH_3)_2$ | CH | |

TABLE 1-continued

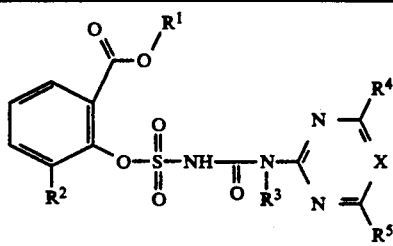

| Example No. | R¹ | R² | R³ | R⁴ | R⁵ | X | Melting Point [°C.] |
|---|---|---|---|---|---|---|---|
| 71 | C₂H₅ | " | H | OCH₃ | OCH₃ | CH | |
| 72 | " | " | H | OCH₃ | CH₃ | CH | |
| 73 | " | " | H | CH₃ | CH₃ | CH | |
| 74 | " | " | H | OCH₃ | Cl | CH | |
| 75 | " | " | H | OCH₃ | OCH₃ | N | |
| 76 | " | " | H | OCH₃ | CH₃ | N | |
| 77 | C₃H₇ | " | H | OCH₃ | OCH₃ | CH | |
| 78 | " | " | H | OCH₃ | CH₃ | CH | |
| 79 | " | " | H | OCH₃ | CH₃ | N | |
| 80 | C₄H₉ | " | H | OCH₃ | OCH₃ | CH | |
| 81 | " | " | H | OCH₃ | CH₃ | CH | |
| 82 | " | " | H | OCH₃ | CH₃ | N | |
| 83 | CH₃ | " | CH₃ | OCH₃ | OCH₃ | CH | |
| 84 | " | " | CH₃ | OCH₃ | CH₃ | CH | |
| 85 | " | " | CH₃ | OCH₃ | CH₃ | N | |
| 86 | " | " | CH₃ | OCH₃ | Cl | CH | |
| 87 | " | " | CH₃ | OCF₂H | OCF₂H | CH | |
| 88 | " | " | CH₃ | CH₃ | CH₃ | CH | |
| 89 | C₂H₅ | " | CH₃ | OCH₃ | OCH₃ | CH | |
| 90 | " | " | CH₃ | OCH₃ | CH₃ | CH | |
| 91 | CH₃ | " | H | OCH₃ | OCH₃ | CH | 134–135 |
| 92 | " | " | H | CH₃ | Cl | CH | |
| 93 | CH₃ | C₂H₅ | H | CH₃ | CH₃ | CH | |
| 94 | " | " | H | OCH₃ | CH₃ | CH | 140–141 |
| 95 | " | " | H | CH₃ | CH₃ | N | |
| 96 | " | " | H | OCH₃ | CH₃ | N | |
| 97 | " | " | H | OCH₃ | OCH₃ | N | |
| 98 | " | " | H | OCH₃ | Cl | CH | |
| 99 | " | " | H | OCF₂H | CH₃ | CH | |
| 100 | " | " | H | OCF₂H | OCF₂H | CH | |
| 101 | " | " | H | OCH₃ | Br | CH | |
| 102 | " | " | H | OCH₃ | OC₂H₅ | CH | |
| 103 | " | " | H | OCH₃ | SCH₃ | CH | |
| 104 | " | " | H | OCH₃ | OC₂H₅ | N | |
| 105 | " | " | H | OCH₃ | OC₃H₇ | CH | |
| 106 | " | " | H | OCH₃ | Cl | N | |
| 107 | " | " | H | Cl | OC₂H₅ | CH | |
| 108 | " | " | H | OC₂H₅ | OC₂H₅ | CH | |
| 109 | " | " | H | C₂H₅ | OCH₃ | CH | |
| 110 | " | " | H | CF₃ | OCH₃ | CH | |
| 111 | " | " | H | OCH₂CF₃ | CH₃ | CH | |
| 112 | " | " | H | OCH₂CF₃ | OCH₃ | CH | |
| 113 | " | " | H | OCH₂CF₃ | OCH₂CF₃ | CH | |
| 114 | " | " | H | OCH₂CF₃ | OCH₃ | N | |
| 115 | " | " | H | OCH₃ | CH(OCH₃)₂ | CH | |
| 116 | C₂H₅ | " | H | OCH₃ | OCH₃ | CH | |
| 117 | " | " | H | OCH₃ | CH₃ | CH | |
| 118 | " | " | H | CH₃ | CH₃ | CH | |
| 119 | " | " | H | OCH₃ | Cl | CH | |
| 120 | " | " | H | OCH₃ | OCH₃ | N | |
| 121 | " | " | H | OCH₃ | CH₃ | N | |
| 122 | C₃H₇ | " | H | OCH₃ | OCH₃ | CH | |
| 123 | " | " | H | OCH₃ | CH₃ | CH | |
| 124 | " | " | H | OCH₃ | CH₃ | N | |
| 125 | C₄H₉ | " | H | OCH₃ | OCH₃ | CH | |
| 126 | " | " | H | OCH₃ | CH₃ | CH | |
| 127 | " | " | H | OCH₃ | CH₃ | N | |
| 128 | CH₃ | " | CH₃ | OCH₃ | OCH₃ | CH | |
| 129 | " | " | CH₃ | OCH₃ | CH₃ | CH | |
| 130 | " | " | CH₃ | OCH₃ | CH₃ | N | |
| 131 | " | " | CH₃ | OCH₃ | Cl | CH | |
| 132 | " | " | CH₃ | OCF₂H | OCF₂H | CH | |
| 133 | " | " | CH₃ | CH₃ | CH₃ | CH | |
| 134 | C₂H₅ | " | CH₃ | OCH₃ | OCH₃ | CH | |
| 135 | " | " | CH₃ | OCH₃ | CH₃ | CH | |
| 136 | CH₃ | " | H | OCH₃ | OCH₃ | CH | 137–138 |
| 137 | " | " | H | CH₃ | Cl | CH | |

TABLE 1-continued

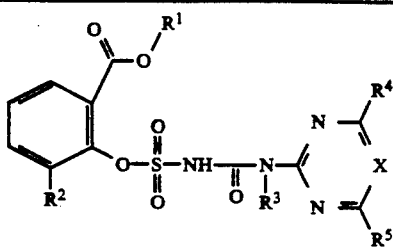

| Example No. | $R^1$ | $R^2$ | $R^3$ | $R^4$ | $R^5$ | X | Melting Point [°C.] |
|---|---|---|---|---|---|---|---|
| 138 | CH₃ | C₃H₇ | H | CH₃ | CH₃ | CH | |
| 139 | " | " | H | OCH₃ | CH₃ | CH | |
| 140 | " | " | H | CH₃ | CH₃ | N | |
| 141 | " | " | H | OCH₃ | CH₃ | N | |
| 142 | " | " | H | OCH₃ | OCH₃ | N | |
| 143 | " | " | H | OCH₃ | Cl | CH | |
| 144 | " | " | H | OCF₂H | CH₃ | CH | |
| 145 | " | " | H | OCF₂H | OCF₂H | CH | |
| 146 | " | " | H | OCH₃ | Br | CH | |
| 147 | " | " | H | OCH₃ | OC₂H₅ | CH | |
| 148 | " | " | H | OCH₃ | SCH₃ | CH | |
| 149 | " | " | H | OCH₃ | OC₂H₅ | N | |
| 150 | " | " | H | OCH₃ | OC₃H₇ | CH | |
| 151 | " | " | H | OCH₃ | Cl | N | |
| 152 | " | " | H | Cl | OC₂H₅ | CH | |
| 153 | " | " | H | OC₂H₅ | OC₂H₅ | CH | |
| 154 | " | " | H | C₂H₅ | OCH₃ | CH | |
| 155 | " | " | H | CF₃ | OCH₃ | CH | |
| 156 | " | " | H | OCH₂CF₃ | CH₃ | CH | |
| 157 | " | " | H | OCH₂CF₃ | OCH₃ | CH | |
| 158 | " | " | H | OCH₂CF₃ | OCH₂CF₃ | CH | |
| 159 | " | " | H | OCH₂CF₃ | OCH₃ | N | |
| 160 | " | " | H | OCH₃ | CH(OCH₃)₂ | CH | |
| 161 | C₂H₅ | " | H | OCH₃ | OCH₃ | CH | |
| 162 | " | " | H | OCH₃ | CH₃ | CH | |
| 163 | " | " | H | CH₃ | CH₃ | CH | |
| 164 | " | " | H | OCH₃ | Cl | CH | |
| 165 | " | " | H | OCH₃ | OCH₃ | N | |
| 166 | " | " | H | OCH₃ | CH₃ | N | |
| 167 | C₃H₇ | " | H | OCH₃ | OCH₃ | CH | |
| 168 | " | " | H | OCH₃ | CH₃ | CH | |
| 169 | " | " | H | OCH₃ | CH₃ | N | |
| 170 | C₄H₉ | " | H | OCH₃ | OCH₃ | CH | |
| 171 | " | " | H | OCH₃ | CH₃ | CH | |
| 172 | " | " | H | OCH₃ | CH₃ | N | |
| 173 | CH₃ | " | CH₃ | OCH₃ | OCH₃ | CH | |
| 174 | " | " | CH₃ | OCH₃ | CH₃ | CH | |
| 175 | " | " | CH₃ | OCH₃ | CH₃ | N | |
| 176 | " | " | CH₃ | OCH₃ | Cl | CH | |
| 177 | " | " | CH₃ | OCF₂H | OCF₂H | CH | |
| 178 | " | " | CH₃ | CH₃ | CH₃ | CH | |
| 179 | C₂H₅ | " | CH₃ | OCH₃ | OCH₃ | CH | |
| 180 | " | " | CH₃ | OCH₃ | CH₃ | CH | |
| 181 | CH₃ | " | H | OCH₃ | OCH₃ | CH | |
| 182 | " | " | H | CH₃ | Cl | CH | |

BIOLOGICAL EXAMPLES

The damage to weed plants and the crop plant tolerance were rated in accordance with a code in which the activity is expressed by numerical values from 0 to 5. In this code:

0 = no action
1 = 0 to 20% action or damage
2 = 20 to 40% action or damage
3 = 40 to 60% action or damage
4 = 60 to 80% action or damage
5 = 80 to 100% action or damage 1. Action on weeds by the pre-emergence method Seeds or pieces of rhizome of mono- and dicotyledon weed plants were laid out in sandy loam soil in plastic pots and covered with soil. The compounds according to the invention, formulated in the form of wettable powders or emulsion concentrates, were then applied in various dosages to the surface of the covering soil as aqueous suspension or emulsions with a water application amount, when converted, of 600 to 800 1/ha.

After the treatment, the pots were placed in a greenhouse and kept under good growth conditions for the weeds. Visual rating of the plants or the emergence damage was performed after the emergence of the test plants after an experimental period of 3 to 4 weeks in comparison with untreated controls. As the rating values in Table 2 show, the compounds according to the invention have a good herbicidal pre-emergence activity against a broad spectrum of gramineous weeds and broad-leaved weeds.

2. Action on weeds by the post-emergence method

Seeds or pieces of rhizome of mono- and dicotyledon weeds were laid out in sandy loam soil in plastic pots, covered with soil and grown in a greenhouse under good growth conditions. Three weeks after sowing, the test plants were treated in the three-leaf stage.

The compounds according to the invention, formulated as wettable powders or as emulsion concentrates, were sprayed in various dosages on to the green parts of the plants with a water application amount, when converted, of 600 to 800 l/ha, and after the test plants had stood in a greenhouse under optimum growth conditions for about 3 to 4 weeks, the action of the preparations was rated visually in comparison with untreated controls.

The agents according to the invention also exhibit a good herbicidal activity against a broad spectrum of economically important gramineous weeds and broad-leaved weeds by the post-emergence method (Table 3).

3. Crop plant tolerance

In further experiments in the greenhouse, seeds of a relatively large number of crop plants and weeds were laid out in sandy loam soil and covered with soil.

Some of the pots were treated immediately as described under 1., and the remainder were placed in a greenhouse until the plants had developed two to three proper leaves, and were then sprayed with the substances according to the invention in various dosages, as described under 2.

Four to five weeks after the application and standing in the greenhouse, it was ascertained by means of visual rating that the compounds according to the invention left dicotyledon crops, such as, for example, soya, cotton, rape, sugar beet and potatoes, undamaged when used by the pre- and post-emergence method, even at high dosages of active compound. Some substances moreover also spared gramineous crops, such as, for example, barley, wheat, rye, sorghum, maize or rice. The compounds of the formula I thus have a high selectivity when used for controlling undesirable plant growth in agricultural crops.

TABLE 2

| Example No. | Dose kg of a.i./ha | Pre-emergence action Herbicidal action | | | |
|---|---|---|---|---|---|
| | | SIAL | CRSE | LOMU | ECCR |
| 2 | 0.3 | 5 | 5 | 2 | 5 |
| 3 | 0.3 | 5 | 5 | 5 | 5 |
| 4 | 0.3 | 5 | 5 | 5 | 5 |
| 5 | 0.3 | 5 | 5 | 5 | 5 |
| 7 | 0.3 | 5 | 5 | 5 | 5 |
| 9 | 0.3 | 5 | 5 | 2 | 4 |
| 42 | 0.3 | 5 | 5 | 5 | 5 |
| 136 | 0.3 | 5 | 5 | 3 | 5 |
| 94 | 0.3 | 5 | 5 | 5 | 5 |
| 91 | 0.3 | 5 | 5 | 2 | 5 |
| 49 | 0.3 | 5 | 5 | 5 | 5 |
| 37 | 0.3 | 5 | 5 | 3 | — |
| 38 | 0.3 | 5 | 5 | 4 | — |
| 40 | 0.3 | 5 | 5 | 2 | 4 |

TABLE 3

| Example No. | Dose kg of a.i./ha | Post-emergence action Herbicidal action | | | |
|---|---|---|---|---|---|
| | | SIAL | CRSE | LOMU | ECCR |
| 2 | 0.3 | 5 | 5 | 3 | 5 |
| 3 | 0.3 | 5 | 5 | 5 | 2 |
| 4 | 0.3 | 5 | 5 | 5 | 4 |
| 5 | 0.3 | 5 | 5 | 5 | 5 |
| 7 | 0.3 | 5 | 5 | 3 | 1 |
| 9 | 0.3 | 5 | 5 | 3 | 2 |
| 25 | 0.3 | 5 | 2 | 2 | 1 |
| 42 | 0.3 | 5 | 5 | 3 | 4 |
| 136 | 0.3 | 5 | 5 | 3 | 4 |
| 94 | 0.3 | 5 | 5 | 5 | 5 |
| 91 | 0.3 | 5 | 5 | 3 | 5 |
| 49 | 0.3 | 5 | 5 | 4 | 5 |
| 37 | 0.3 | 5 | 5 | 3 | 3 |
| 38 | 0.3 | 5 | 5 | 2 | 3 |
| 40 | 0.3 | 5 | 5 | 1 | 2 |

Abbreviations:
SIAL = *Sinapis alba*
CRSE = *Chrysanthemum segetum*
LOMU = *Lolium multiflorum*
ECCR = *Echinochloa crus-galli*
a.i. = active ingredient

We claim:

1. A compound of formula I or a salt thereof

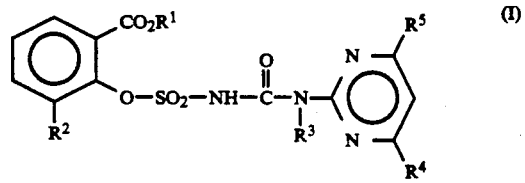

in which
$R^1$ is ($C_1$–$C_4$) alkyl;
$R^2$ is chloro, methoxy or ethyl;
$R^3$ is hydrogen;
$R^4$ is methoxy or methyl; and
$R^5$ is methoxy or methyl.

2. A compound as claimed in claim 1, wherein $R^1$ is methyl, $R^4$ is methoxy and $R^5$ is methoxy.

3. A compound as claimed in claim 2, wherein $R^2$ is chloro.

4. A compound as claimed in claim 2, wherein $R^2$ is methoxy.

5. A compound as claimed in claim 2, wherein $R^2$ is ethyl.

6. A compound as claimed in claim 1, in which $R^1$ is methyl, $R^2$ is methoxy, $R^3$ is hydrogen, $R^4$ is methoxy, and $R^5$ is methoxy.

7. A compound as claimed in claim 1, in which $R^1$ is n-butyl, $R^2$ is methoxy, $R^3$ is hydrogen, and $R^4$ and $R^5$ are methoxy.

8. A compound as claimed in claim 1, in which $R^1$ is n-butyl, $R^2$ is methoxy, $R^3$ is hydrogen, $R^4$ is methoxy, and $R^5$ is methyl.

9. A compound as claimed in claim 1, in which $R^1$ is methyl, $R^2$ is methoxy, $R^3$ is methyl, and $R^4$ and $R^5$ are methoxy.

10. A compound as claimed in claim 1, in which $R^1$ is methyl, $R^2$ is methoxy, $R^3$ is hydrogen, $R^4$ is methoxy, and $R^5$ is methyl.

11. A compound as claimed in claim 1, in which $R^1$ is methyl, $R^2$ is Cl, $R^3$ is hydrogen, and $R^4$ and $R^5$ are methoxy.

12. A compound as claimed in claim 1, in which $R^1$ is methyl, $R^2$ is ethyl, $R^3$ is hydrogen, and $R^4$ and $R^5$ are methoxy.

13. A herbicidal composition which contains a compound of the formula (I) as claimed in claim 1 or a salt thereof and customary inert formulation auxiliaries.

14. A plant growth-regulating composition which contains a compound of the formula (I) as claimed in claim 1, or a salt thereof and customary inert formulation auxiliaries.

15. A method for controlling undesirable plants which comprises applying an effective amount of a compound of the formula I or salt thereof as claimed in claim 1, to these plants or their cultivation areas.

16. A method of regulating plant growth, which comprises applying an effective amount of a compound of the formula I or a salt thereof as claimed in claim 1, to these plants or their cultivation areas.

* * * * *